(12) United States Patent
Ikemoto (10) Patent No.: US 10,131,661 B2
(45) Date of Patent: Nov. 20, 2018

(54) HIGH-SOLUBILITY ACETONE-ADDED PYRROLOQUINOLINE QUINONE SALT

(71) Applicant: Mitsubishi Gas Chemical Company, Inc., Chiyoda-ku (JP)

(72) Inventor: Kazuto Ikemoto, Niigata (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 0 days.

(21) Appl. No.: 15/544,403

(22) PCT Filed: Dec. 15, 2015

(86) PCT No.: PCT/JP2015/085064
§ 371 (c)(1),
(2) Date: Jul. 18, 2017

(87) PCT Pub. No.: WO2016/117242
PCT Pub. Date: Jul. 28, 2016

(65) Prior Publication Data
US 2018/0009803 A1    Jan. 11, 2018

(30) Foreign Application Priority Data

Jan. 19, 2015    (JP) .................. 2015-007414

(51) Int. Cl.
*C07D 471/04*    (2006.01)
*A61K 31/4745*    (2006.01)

(52) U.S. Cl.
CPC ........ *C07D 471/04* (2013.01); *A61K 31/4745* (2013.01); *C07B 2200/13* (2013.01)

(58) Field of Classification Search
CPC ............. C07D 471/04; C07B 2200/13; A61K 31/4745
USPC ......................................... 546/84
See application file for complete search history.

(56) References Cited

U.S. PATENT DOCUMENTS

| | | | |
|---|---|---|---|
| 9,604,979 B2 * | 3/2017 | Ikemoto | ............... C07D 471/04 |
| 2014/0128609 A1 * | 5/2014 | Ikemoto | ................... C12P 7/66 546/84 |
| 2015/0203488 A1 * | 7/2015 | Ikemoto | ............... A61K 8/4926 424/94.1 |

FOREIGN PATENT DOCUMENTS

| | | | | |
|---|---|---|---|---|
| JP | 6-126259 A | 5/1994 | | |
| WO | WO-2013051414 A1 * | 4/2013 | | ........... C07D 47/104 |

OTHER PUBLICATIONS

Shinobu Itoh et al , C4 and C5 adducts of Cofactor PQQ (Year: 1993).*
PQQ salt v PQQ, Michael Rucker (Year: 2011).*
Corey et al, Total Synthesis of the Quinonoid Alcohol Dehydrogenase Coenzyme (1) of Methylotrophic Bacteria (Year: 1981).*
Translation of WO 2013051414 (Year: 2013).*
International Search Report dated Mar. 15, 2016, in PCT/JP2015/085064 filed Dec. 15, 2015.
Salisbury, S.A. et al., "A novel coenzyme from bacterial primary alcohol dehydrogenases", NATURE, vol. 280 , No. 5725, (1979), pp. 843-844.
Corey, et al., "Total synthesis of quinonoid alcohol dehydrogenase coenzyme (1) of methylatrophic bacteria", Journal of the American Chemical Society, vol. 103, No. 18, (1981), pp. 5599-5600.
Gainor et al., "Total synthesis of methoxatin, the coenzyme of methanol dehydrognase and glucose degydrogenase", Journal of Organic Chemistry, vol. 46, No. 21, (1981), pp. 4317-4319.

* cited by examiner

*Primary Examiner* — Rita J Desai
(74) *Attorney, Agent, or Firm* — Oblon, McClelland, Maier & Neustadt, L.L.P.

(57) ABSTRACT

There are provided an alkali metal salt of 5-hydroxy-4-oxo-5-(2-oxopropyl)-4,5-dihydro-1H-pyrrolo[2,3-f]quinoline-2,7,9-tricarboxylic acid, a method for producing the alkali metal salt, and a cocrystal comprising the alkali metal salt.

17 Claims, 2 Drawing Sheets

HIGH-SOLUBILITY ACETONE-ADDED PYRROLOQUINOLINE QUINONE SALT

TECHNICAL FIELD

The present invention relates to an alkali metal salt of 5-Hydroxy-4-oxo-5-(2-oxopropyl)-4,5-dihydro-1H-pyrrolo[2,3-f]quinoline-2,7,9-tricarboxylic acid, a cocrystal, and a method for producing the same.

BACKGROUND ART

5-Hydroxy-4-oxo-5-(2-oxopropyl)-4,5-dihydro-1H-pyrrolo[2,3-f]quinoline-2,7,9-tricarboxylic acid (hereinafter, referred to also as "HOP") is a compound represented by the following formula (2).

(2)

This substance is called an acetone adduct of pyrroloquinoline quinone in some cases. The structure of HOP is used for the determination of the structure of pyrroloquinoline quinone (for example, see Non Patent Literature 1). HOP is a white to yellow substance.

CITATION LIST

Patent Literature

Non Patent Literature 1: Nature, 1979, 280, 843-844

SUMMARY OF INVENTION

Technical Problem

The cell proliferative activity, in the case of substances are used as culture medium components, cosmetics or pharmaceuticals, is a function said to be important in order to enhance the productivity of cultivation, or in order to enhance metabolism of skins. As a substance having such cell proliferative activity, pyrroloquinoline quinone (PQQ) is known.

Pyrroloquinoline quinone, however, has problems of being poor in solubility to water, and being liable to cause deterioration accompanied by color change and thus being poor in stability. Then, there has been demanded a compound which can be anticipated to have the same working-effect as pyrroloquinoline quinone, and is excellent in solubility and excellent in deterioration resistance and color change resistance.

Here, HOP being an aldol adduct of PQQ, since relatively simply and easily returning to pyrroloquinoline quinone, is anticipated to be used as a generating agent of pyrroloquinoline quinone. Although it is a problem that HOP itself has low solubility to water similarly to PQQ, if a HOP derivative has a working-effect equal to that of PQQ, and is excellent in solubility and excellent in deterioration resistance and color change resistance, there can be anticipated applications thereof to uses as culture medium components, cosmetics, pharmaceuticals and the like. With respect to this point, by studies by the present inventor, it has been made clear that HOP has a cell proliferative activity, and it has been found that even in the case where HOP is used in a high concentration, the reduction in the cell proliferation rate to the concentration is more hardly caused than in the case of PQQ. Further, there is no report so far on an alkali metal salt of HOP, and on a cocrystal comprising an alkali metal salt of HOP. Particularly, it has been made clear in the course of studies by the present inventor that HOP is easily colored by a change in pH; and there is such a problem that with respect to an isolation method of the alkali metal salt, it is difficult to isolate the alkali metal salt as a clean solid by a simple method of reacting an alkali metal hydroxide with the tricarboxylic acid in an aqueous solution and removing water.

The present invention has been achieved in consideration of the above problematic point, and has an object to provide a novel alkali metal salt of HOP, a method for producing the alkali metal salt of HOP, and a novel cocrystal comprising the alkali metal salt of HOP.

Solution to Problem

The present inventor has carried out exhaustive studies in order to solve the above problem. As a result, it has been found that HOP has a cell proliferative activity, is lower in the reactivity with other substances such as reducing agents and amino acids than pyrroloquinoline quinone, and is stable and hardly deteriorated. It has further been found that by turning HOP to an alkali metal salt thereof, there is a method capable of stably producing the salt remarkably improved in solubility and suppressed in the coloration; and it has been found that by items indicated in the below, the above problem can be solved.

That is, the present invention is as follows.

[1]
An alkali metal salt represented by following formula (1):

(1)

wherein $M_1$, $M_2$ and $M_3$ each independently represent hydrogen atom or an alkali metal, and one or more of $M_1$, $M_2$ and $M_3$ each independently represent the alkali metal.

[2] The alkali metal salt according to [1], wherein two or more of $M_1$, $M_2$ and $M_3$ each independently represent the alkali metal.

[3]
The alkali metal salt according to [1] or [2], wherein the alkali metal is sodium.
[4]
A cocrystal, comprising:
the alkali metal salt according to any one of [1] to [3], and an alkali metal hydrogen carbonate salt and/or an alkali metal carbonate salt.
[5]
A method for producing an alkali metal salt of 5-hydroxy-4-oxo-5-(2-oxopropyl)-4,5-dihydro-1H-pyrrolo[2,3-f]quinoline-2,7,9-tricarboxylic acid comprising a step of:
mixing 5-hydroxy-4-oxo-5-(2-oxopropyl)-4,5-dihydro-1H-pyrrolo[2,3-f]quinoline-2,7,9-tricarboxylic acid with an alkali metal hydrogen carbonate salt and/or an alkali metal carbonate salt in a solvent.
[6]
The method according to [5], wherein the solvent comprises water.
[7]
The method according to [5], wherein the solvent comprises an organic solvent.

Advantageous Effects of Invention

The present invention can provide a HOP alkali metal salt and a method for stably producing the HOP alkali metal salt.

DESCRIPTION OF EMBODIMENTS

Hereinafter, an embodiment (hereinafter, referred to as "the present embodiment") to carry out the present invention will be described in detail, but the present invention is not limited thereto, and various changes and modifications may be made without departing from its gist.
[Alkali Metal Salt]
An alkali metal salt of the present embodiment is represented by the following formula (1). Here, in the present description, the alkali metal salt of the present embodiment is referred to also as a "HOP alkali metal salt", and a compound in which all of $M_1$, $M_2$ and $M_3$ show hydrogen atoms is referred to also as a "HOP free form".

$$\text{(1)}$$

wherein $M_1$, $M_2$ and $M_3$ each independently represent hydrogen atom or an alkali metal, and one or more of $M_1$, $M_2$ and $M_3$ each independently represent an alkali metal.

One or more of $M_1$, $M_2$ and $M_3$ are alkali metals, and it is preferable that two or three of $M_1$, $M_2$ and $M_3$ be alkali metals. When one or more of $M_1$, $M_2$ and $M_3$ are alkali metals, the solubility of a HOP alkali metal salt to water is more improved. Specifically, with the increasing number of replacement of alkali metals, pH moves to an alkali side and the solubility is likely to rise, the HOP alkali metal salt in which the number of replacement of alkali metals is 3 has a highest solubility. The number of replacement of alkali metals of a HOP alkali metal salt conceivably varies depending on pH in crystallization in a solvent, and the number of replacement rises as the pH moves from acidic to alkaline. Further the coloration of materials mixed with the HOP alkali metal salt can be more suppressed. Hence, the HOP alkali metal salt of the present embodiment becomes one whose use applications are hardly restricted.

Here, the HOP alkali metal salt of the present embodiment, as long as one or more of $M_1$, $M_2$ and $M_3$ are alkali metals, may be, for example, a single compound in which only $M_1$ is an alkali metal, a mixture comprising two or more compounds of a compound in which only $M_1$ is an alkali metal and a compound in which only $M_2$ is an alkali metal, or the like, or a mixture comprising two or more compounds of a compound in which only $M_1$ is an alkali metal and a compound in which $M_2$ and $M_3$ are alkali metals. In the case where the HOP alkali metal salt of the present embodiment is a mixture, the molar number of alkali metals comprised in per 1 mol of the HOP alkali metal salt as the whole mixture is preferably 1 mol or more, more preferably 2 to 3 mol, and still more preferably 2.5 to 2.9 mol. When the molar number of alkali metals comprised in 1 mol of the HOP alkali metal salt is in the above range, it is likely that the solubility is higher and the color change is more suppressed.

The alkali metal is not especially limited, but is preferably Li, Na and K, more preferably Na and K, and still more preferably Na. By using such an alkali metal, the solubility of the HOP alkali metal salt to water is likely to be improved. Particularly since Na and K are ions present normally in living bodies, HOP alkali metal salts comprising Na and/or K can be used safely as effective components of foods, feeds, pharmaceuticals, quasi-drugs, cosmetics and the like for human or for animals.

Among HOP alkali metal salts, especially preferable are a HOP trisodium salt, a HOP tripotassium salt, a HOP disodium salt and a HOP dipotassium salt. Such HOP alkali metal salts not only are high in the solubility to water, but also can be used safely as effective components of foods, feeds, pharmaceuticals, quasi-drugs, cosmetics and the like for human or for animals.

Since the HOP alkali metal salt has a —$COOM_1$ group, a —$COOM_2$ group, a $COOM_3$ group and a —OH group, and one or more of $M_1$, $M_2$ and $M_3$ are alkali metals, the HOP alkali metal salt has a maximum of three functional groups capable of releasing a hydrogen ion. Among these functional groups, a hydrogen ion may be released from any functional group and the functional group may turn to a —$COO^-$ group or a —$O^-$ group. Here, the releasing state of hydrogen ions has a possibility of changing also depending on the crystal state of the HOP alkali metal salt.

Further the HOP alkali metal salt of the present embodiment may be a hydrated salt in which one or two or more water molecules hydrate, or a solvated salt in which one or two or more solvent molecules solvate.

[Cocrystal]

A cocrystal (hereinafter, referred to also as a "HOP cocrystal") of the present embodiment comprises the above HOP alkali metal salt and an alkali metal hydrogen carbonate salt and/or an alkali metal carbonate salt. The HOP cocrystal is high in the solubility to water, and is higher in stability and more hardly changed in color than the HOP alkali metal salt. Hence, the HOP cocrystal can suitably be used in applications such as foods, feeds, pharmaceuticals, quasi-drugs and cosmetics for human or for animals.

The alkali metal comprised in the alkali metal hydrogen carbonate salt and the alkali metal carbonate salt is preferably Li, Na and K, more preferably Na and K, and still more preferably Na. By using such an alkali metal, the solubility of the HOP cocrystal to water is likely to be more improved. Particularly since Na and K are ions present normally in living bodies, HOP cocrystals comprising Na and/or K can be used safely as effective components of foods, feeds, pharmaceuticals, quasi-drugs, cosmetics and the like for human or for animals.

The content of the alkali metal hydrogen carbonate salt in the HOP cocrystal is, with respect to 1 mol of the HOP alkali metal salt, preferably 1 to 4 mol, and more preferably 2 to 3 mol. Further the content of the alkali metal carbonate salt in the HOP cocrystal is, with respect to 1 mol of the HOP alkali metal salt, preferably 1 to 3 mol, more preferably 1 to 2 mol, and still more preferably 1 to 1.5 mol.

A HOP trialkali metal hydrogen carbonate cocrystal is more stable and more hardly changed in color than a HOP trialkali metal salt. Hence, the HOP trialkali metal hydrogen carbonate cocrystal has the advantage of being a substance holding the solubility high and being stable. Here, although this HOP cocrystal exists in a solid state, in the case of being dissolved in water, the carbonate and the hydrogen carbonate escape as carbon dioxide gas, and the above HOP cocrystal can be handled nearly similarly to the above HOP alkali metal salt. The impartment of the physiological activity by carbon dioxide gas can be cited as an advantage in the point that the cocrystal generates bubbling of the carbon dioxide gas when being contacted with water, and the dissolution of the powder in a liquid is promoted.

[Method for Producing the HOP Alkali Metal Salt]

A method for producing the HOP alkali metal salt of the present embodiment is not especially limited as long as being a method comprising a mixing step of mixing 5-hydroxy-4-oxo-5-(2-oxopropyl)-4,5-dihydro-1H-pyrrolo[2,3-f]quinoline-2,7,9-tricarboxylic acid with an alkali metal hydrogen carbonate salt and/or an alkali metal carbonate salt in a solvent.

[Production Step of the HOP Free Form]

Before description of the above step, a production step of the HOP free form will be described. The production method of the HOP free form is not especially limited, but example thereof includes a method in which pyrroloquinoline quinone or its salt is mixed with acetone and subjected to an aldol reaction. The aldol reaction may be carried out in any of a solution, a suspension state or a gel state, but is preferably carried out in water.

The reaction temperature is preferably 0 to 180° C., and more preferably 5 to 130° C. The reaction temperature of 0° C. or more is industrially preferable, since the reaction velocity is improved Further the reaction temperature of 180° C. or less is preferable, since a necessary pressure resistance of a reaction vessel can be lowered and the use of a high-pressure-resistant high-price pressure vessel can be eliminated.

The concentration of the pyrroloquinoline quinone in a reaction system is preferably 0.1 to 30% by mass, more preferably 0.5 to 25% by mass, and still more preferably 1 to 20% by mass. Further the use amount of acetone in the reaction system is, with respect to 1 part by mass of the pyrroloquinoline quinone, preferably 0.3 to 50 parts by mass, more preferably 0.5 to 45 parts by mass, and still more preferably 1 to 40 parts by mass.

The above aldol reaction is initiated by making the pH of the system to be alkaline in higher than 7; after 3 days to 1 week, the reaction can be terminated while a HOP free form is being deposited by making the pH of the system to be acidic in 1 to 4. Thereafter, the deposited HOP free form is filtered off to thereby obtain a HOP free form. A base to make the alkalinity is not especially limited, but examples thereof include sodium hydroxide and potassium hydroxide. An acid to make the acidity is not especially limited, but there can be used, for example, hydrochloric acid, sulfuric acid, nitric acid, phosphoric acid, perchloric acid, acetic acid, citric acid, oxalic acid, succinic acid and tartaric acid.

The advancement of the aldol reaction can be judged by changes in the color of the system. The aldol reaction can be confirmed, for example, by checking a change in color from a reddish color which a solution has at first to colorless or yellow. Besides, as more quantitative methods, there can also be used common analysis means such as liquid chromatography and paper chromatography.

Further the HOP free form obtained as described above may further be refined by using a common method such as recrystallization or chromatography. Further a higher-purity HOP free form can be obtained by making the pH to be 2 or less by adding an acid to an aqueous solution comprising the HOP free form obtained by the above reaction. The acid to be used at this time is not especially limited, but there can be used, for example, hydrochloric acid, sulfuric acid, nitric acid, phosphoric acid, perchloric acid, acetic acid, citric acid, oxalic acid, succinic acid and tartaric acid. The obtained HOP free form comprises no alkali metal, and can be used as a raw material of HOP salts.

[Mixing Step]

The HOP alkali metal salt of the present embodiment can be produced by mixing the HOP free form with an alkali metal carbonate salt and/or an alkali metal hydrogen carbonate salt in a solvent, and thereafter refining the mixture. The mixing temperature is preferably 0 to 50° C., more preferably 5 to 45° C., and still more preferably 10 to 40° C. Here, as the HOP free form to be used in the mixing step, it is preferable to use a HOP free form refined up to 90% or more in purity in the production step of the HOP free form.

The HOP alkali metal salt, when being under an acidic condition and with a sufficient solvent, is likely to be hardly changed in color. Hence, also an alkali metal hydroxide and an alkali metal alkoxide can auxiliarily be mixed in combination.

A solvent to be used in the mixing step is not especially limited, but examples thereof include water, organic solvents and mixed solvents of water and an organic solvent. When the solvent comprises water, the yield of the HOP alkali metal salt is likely to be more improved. Further when the solvent comprises an organic solvent, the yield of the HOP cocrystal described later is likely to be more improved. In the method for producing the HOP alkali metal salt, the content of water comprised in the solvent is, with respect to 100% by mass of the solvent, 90% by mass or more, and more preferably 95% by mass or more.

Here, the organic solvent is preferably a water-soluble organic solvent. The water-soluble organic solvent specifically includes acetone; alcohols such as methanol, ethanol, isopropanol and 2-propanol; acetonitrile; glycols such as propylene glycol; and glycerol.

The number of replacement of an alkali metal salt can be controlled by the molar ratio of a HOP free form and an alkali metal carbonate salt and/or an alkali metal hydrogen carbonate salt. For example, a HOP alkali metal salt in which two of $M_1$, $M_2$ and $M_3$ are alkali metals can easily be obtained by mixing 1 mol of a HOP free form with 2 mol of an alkali metal hydrogen carbonate salt in a solvent, and removing water under reduced pressure.

A refining method after the reaction is not especially limited, but examples thereof include removal of the solvent and recrystallization. The salt can also be deposited by salting out or addition of a water-soluble organic solvent. For example, in the case of a HOP alkali metal salt in which three of $M_1$, $M_2$ and $M_3$ are alkali metals, since the HOP alkali metal salt is easily changed in color, it is preferable to subject the HOP alkali metal salt to a refining treatment at a low temperature. The refining treatment temperature in this case is preferably 30° C. or less, and more preferably 20° C. or less.

Further when the deposition is carried out by removal of the solvent, in order to suppress the color change of the HOP alkali metal salt or the HOP cocrystal, it is preferable to carry out the solvent removal in a short time.

Further from the viewpoint of suppressing the color change, after the mixing step is carried out in an aqueous solvent, it is preferable to add an organic solvent and quickly deposit the HOP alkali metal salt.

In the method for producing a HOP alkali metal salt, in the case where a HOP free form and an alkali metal carbonate salt and/or an alkali metal hydrogen carbonate salt are reacted in water and water content is removed, the molar number of the alkali metal carbonate salt and/or the alkali metal hydrogen carbonate salt to be used in the mixing step is, with respect to 1 mol of the HOP free form, preferably 1 to 3 mol, more preferably 2 to 3 mol, and still more preferably 2 to 2.9 mol. When the molar number of the alkali metal carbonate salt and/or the alkali metal hydrogen carbonate salt is in the above range, it is likely that an obtained HOP alkali metal salt is more suppressed in the color change, and is more improved in the solubility to water.

Further In the method for producing a HOP alkali metal salt, in the case where a HOP free form and an alkali metal carbonate salt and/or an alkali metal hydrogen carbonate salt are reacted in water and an organic solvent is added to thereby deposit the HOP alkali metal salt, the molar number of the alkali metal carbonate salt and/or the alkali metal hydrogen carbonate salt to be used in the mixing step is, with respect to 1 mol of the HOP free form, preferably 1 to 3 mol, and in consideration of the low-temperature processing, more preferably 2.7 to 3 mol.

[Production Method of the Cocrystal]

The cocrystal of the present embodiment can be obtained in the case where the method for producing the HOP alkali metal salt is carried out in a solvent at least comprising an organic solvent. The organic solvent includes the same as in the above.

The solvent may comprise water according to a cocrystal as a target. The content of water comprised in the solvent is preferably such an amount that the alkali metal carbonate salt and/or the alkali metal hydrogen carbonate salt is not completely dissolved and remains in the solvent, and the optimum value thereof differs depending on the charging amount of raw materials. For example, the content of water comprised in the solvent is, with respect to 100% by mass of the solvent, preferably 10% by mass or less, more preferably 7.5% by mass or less, and still more preferably 5% by mass or less. When the water content is in the above range, it is likely that the yield of the cocrystal is more improved and the cocrystal can be obtained well reproducibly.

Hereinafter, a specific example of the method for producing a cocrystal will be described. A HOP free form and an alkali metal compound are mixed in a solvent at least containing an organic solvent. Although the HOP free form is not dissolved in water, by mixing the alkali metal compound therewith, the solubility is raised and the HOP free form comes to be easily dissolved in water. The temperature at this time usable is 0 to 120° C., but preferably 0 to 50° C. Since the HOP free form is generally more easily dissolved in a higher temperature, but is liable to be deteriorated, the mixing at a low temperature is preferable. The mixing is carried out by stirring, which is preferable from the viewpoint of homogeneity. The complete dissolution of the mixture is preferable. The resultant mixture is allowed to stand still for 0.01 to 96 hours, and thereafter, water is removed. The removal can use vacuum drying, spray drying, freeze drying or the like. A HOP salt as a dried powder can be obtained.

[Applications]

The HOP alkali metal salt and the HOP cocrystal of the present embodiment have the cell proliferative activity. Further they can be used as a generating agent of pyrroloquinoline quinone. Hence, the HOP alkali metal salt and the HOP cocrystal of the present embodiment have many pharmacological effects of the functions of pyrroloquinoline quinone, such as anti-cataract action, liver disease preventing and therapeutic action, wound healing action, antiallergic action, reverse transcriptase inhibitory action, glyoxalase I inhibitory action-anticancer action and nerve fiber regeneration.

Therefore, the HOP alkali metal salt and the HOP cocrystal of the present embodiment can be made to be effective components of pharmaceuticals and functional foods. That is, they can be provided in forms of skin external preparations, injections, oral agents, suppositories and the like, and in forms of food and drink daily taken, nutrition reinforcing foods, various types of hospital foods and the like. Here, additives to be used for being prepared so as to be suitable for these forms are not especially limited. For example, liquids are not especially limited, but there can be used, for example, water, sugars such as fructose and glucose, oils such as peanut oil, soybean oil and olive oil, and glycols such as polyethylene glycol and polypropylene glycol. Further as excipients of solid agents such as tablets, capsules and granules are not especially limited, but examples thereof include sugars such as lactose, sucrose and mannitol. Further, lubricants are not especially limited, but examples thereof include kaolin, talc and magnesium stearate; disintegrants include starch and sodium alginate; and binders include polyvinyl alcohol, cellulose and gelatin. Further surfactants are not especially limited, but examples thereof include fatty acid esters. Further plasticizers are not especially limited, but examples thereof include glycerol. Further, as required, there may be added dissolution promoting agents, fillers and the like.

The HOP alkali metal salt and the cocrystal of the present embodiment may be used singly or in combination with other materials. Examples of other materials combinable include vitamins such as a vitamin B group, vitamin C and vitamin E, amino acids, astaxanthin, carotenoids such as α-carotene and β-carotene, ω3 fatty acids such as docosahexaenoic acid and eicosapentaenoic acid, and ω6 fatty acids such as arachidonic acid, but are not limited thereto.

The HOP alkali metal salt of the present embodiment, since being high in solubility and excellent in storage stability, can be stored for a long period and can suitably be used as an effective component of pharmaceuticals and functional foods.

EXAMPLES

Hereinafter, the present embodiment will be described in more detail by way of Examples and Comparative Examples, but the present embodiment is not limited to these Examples and Comparative Examples.

The present Examples used reagents manufactured by Wako Pure Chemical Industries, Ltd., unless otherwise specified. The measurement of the absorbance used a UV spectrum meter UV1800 manufactured by Shimadzu Corp. LC conditions: an absorbance detector used 259 nm as the detection wavelength. An YMC-Pack ODS-A (150 mm, 4.6 mm) column was used at 40° C.; a developing solution used was a 30 mM acetic acid-70 mM ammonium acetate, and the analysis was carried out at a flow rate of 1 mL/min. The apparatus used was an LC2010 (manufactured by Shimadzu Corp.).

Reference Example 1

Production of a HOP Free Form to Become a Raw Material 11.2 g of PQQ disodium (manufactured by Mitsubishi Gas Chemical Co., Ltd., BioPQQ) was added to 1 L of water to thereby prepare an aqueous solution, and NaOH was added to the obtained aqueous solution to thereby make the pH of the aqueous solution to be 9. 200 g of acetone was added to the aqueous solution, when the aqueous solution was then changed in color from red to light yellow in 20 min. Then, hydrochloric acid was added to the aqueous solution to thereby make the pH thereof to be 2.5. Thereafter, the aqueous solution was concentrated until the total amount thereof became 400 g by evaporating water content in the aqueous solution. In the aqueous solution after being concentrated, a yellow solid was deposited. The solid was further dried under reduced pressure to thereby obtain 8.01 g of a solid.
(Analysis of the Alkali Metal)

1 mg of the solid obtained as in the above was dissolved in 1 g of a 1% choline water to thereby obtain a test solution. As a result of an analysis at room temperature (25° C.) of the obtained test solution by using a sodium electrode manufactured by Horiba Ltd., no alkali metal ions were detected. From this, it was confirmed that the obtained solid was a HOP free form.

Example 1

Production of HOP Disodium 0.39 g of the HOP free form, 20 g of water and 0.16 g of sodium hydrogen carbonate were mixed in a flask, when bubbling from the mixed solution was then observed. The mixed solution was at a pH of 4. The mixed solution was stirred at 23° C. for 5 hours; thereafter, the flask was put in a water bath at 35° C., and the pressure was gradually reduced from 200 mbar down to 30 mbar by an evaporator to remove water to thereby obtain a white crystal. Further, the obtained crystal was dried for one night by a vacuum drier. It was confirmed from an alkali metal analysis using a sodium electrode manufactured by Horiba Ltd., and a liquid chromatograph analysis (LC analysis) using an LC2010 (manufactured by Shimadzu Corp.) that 0.47 g of a HOP disodium salt was obtained.

Example 2

Production of HOP Trisodium 0.39 g of the HOP free form, 2 g of water and 0.25 g of sodium hydrogen carbonate were mixed in a flask, when bubbling from the mixed solution was then observed. The mixed solution was subjected to an ultrasonic wave for 5 min, when the solid content in the mixed solution was all dissolved. The resultant solution was at a pH of 7. Thereafter, the flask was put in a water bath at 35° C., and the pressure was gradually reduced from 200 mbar down to 30 mbar by an evaporator to remove water to thereby obtain a light yellow crystal. Further, the obtained crystal was dried for one night by a vacuum drier. It was confirmed from an alkali metal analysis using a sodium electrode manufactured by Horiba Ltd., and a liquid chromatograph analysis (LC analysis) using an LC2010 (manufactured by Shimadzu Corp.) that 0.50 g of HOP trisodium was obtained.

Example 3

Production of HOP 2.5 Sodium 0.78 g of the HOP free form, 4 g of water and 0.42 g of sodium hydrogen carbonate were mixed in a flask, when bubbling from the mixed solution was then observed. The mixed solution was stirred at 23° C. for 1 hour, when the solid content in the mixed solution was all dissolved. The resultant solution was at a pH of 7. Thereafter, the flask was put in a water bath at 35° C., and the pressure was gradually reduced from 200 mbar down to 30 mbar by an evaporator to remove water to thereby obtain a light yellow crystal. Further, the obtained crystal was dried for one night by a vacuum drier. It was confirmed from an alkali metal analysis using a sodium electrode manufactured by Horiba Ltd., and a liquid chromatograph analysis (LC analysis) using an LC2010 (manufactured by Shimadzu Corp.) that 1.00 g of HOP 2.5 sodium was obtained.

Example 4

Production of HOP 2.9 Sodium 0.78 g of the HOP free form, 4 g of water and 0.49 g of sodium hydrogen carbonate were mixed in a flask, when bubbling from the mixed solution was then observed. The mixed solution was stirred at 23° C. for 1 hour, when the solid content in the mixed solution was all dissolved. The resultant solution was at a pH of 7. Thereafter, the flask was put in a water bath at 35° C., and the pressure was gradually reduced from 200 mbar down to 30 mbar by an evaporator to remove water to thereby obtain a light yellow crystal. Further, the obtained crystal was dried for one night by a vacuum drier. It was confirmed from an alkali metal analysis using a sodium electrode manufactured by Horiba Ltd., and a liquid chromatograph analysis (LC analysis) using an LC2010 (manufactured by Shimadzu Corp.) that 0.95 g of HOP 2.9 sodium was obtained.

Example 5

Production of HOP Trisodium by an Organic Solvent Precipitation Method 0.78 g of the HOP free form, 4 g of water and 0.50 g of sodium hydrogen carbonate were mixed in a flask, when bubbling from the mixed solution was then observed. The mixed solution was subjected to an ultrasonic wave for 5 min, when the solid content in the mixed solution was all dissolved. When 36 mL of methanol was added thereto and the resultant was stored in a cooling chamber (4° C.) for one night, a solid was then deposited. The solid was centrifugally separated and taken out to thereby obtain a white crystal. Further, the obtained crystal was dried for one night by a vacuum drier. It was confirmed from an alkali metal analysis using a sodium electrode manufactured by Horiba Ltd., and a liquid chromatograph analysis (LC analysis) using an LC2010 (manufactured by Shimadzu Corp.) that 0.41 g of HOP trisodium was obtained.

Example 6

Production of HOP Tripotassium 0.39 g of the HOP free form, 2 g of water and 0.30 g of potassium hydrogen carbonate were mixed in a flask, when bubbling from the mixed solution was then observed. The mixed solution was stirred at 23° C. for 1 hour, when the solid content in the mixed solution was all dissolved. Thereafter, the flask was put in a water bath at 35° C., and the pressure was gradually reduced from 200 mbar down to 30 mbar by an evaporator to remove water to thereby obtain a gray crystal. Further, the obtained crystal was dried for one night by a vacuum drier. It was confirmed from an alkali metal analysis using a sodium electrode manufactured by Horiba Ltd., and a liquid chromatograph analysis (LC analysis) using an LC2010 (manufactured by Shimadzu Corp.) that 0.55 g of HOP tripotassium was obtained.

Example 7

Production of HOP Dipotassium 0.39 g of the HOP free form, 10 g of water and 0.20 g of potassium hydrogen carbonate were mixed in a flask, when bubbling from the mixed solution was then observed. The mixed solution was stirred at 23° C. for 1 hour, when the solid content in the mixed solution was all dissolved. Thereafter, the flask was put in a water bath at 35° C., and the pressure was gradually reduced from 200 mbar down to 30 mbar by an evaporator to remove water to thereby obtain a light yellow crystal. Further, the obtained crystal was dried for one night by a vacuum drier. It was confirmed from an alkali metal analysis using a sodium electrode manufactured by Horiba Ltd., and a liquid chromatograph analysis (LC analysis) using an LC2010 (manufactured by Shimadzu Corp.) that 0.51 g of HOP dipotassium was obtained.

Example 8

Production of HOP Trilithium 0.39 g of the HOP free form, 2 g of water and 0.11 g of lithium carbonate were mixed in a flask, when bubbling from the mixed solution was then observed. When the mixed solution was stirred at 23° C. for 1 hour, the solid content in the mixed solution was all dissolved. Thereafter, the flask was put in a water bath at 35° C., and the pressure was gradually reduced from 200 mbar down to 30 mbar by an evaporator to remove water to thereby obtain a light yellow crystal. Further, the obtained crystal was dried for one night by a vacuum drier. It was confirmed from an alkali metal analysis using a sodium electrode manufactured by Horiba Ltd., and a liquid chromatograph analysis (LC analysis) using an LC2010 (manufactured by Shimadzu Corp.) that 0.39 g of HOP trilithium was obtained.

Example 9

Production of HOP Dilithium 0.39 g of the HOP free form, 2 g of water and 0.07 g of lithium carbonate were mixed in a flask, when bubbling from the mixed solution was then observed. The mixed solution was stirred at 23° C. for 1 hour. Thereafter, the flask was put in a water bath at 35° C., and the pressure was gradually reduced from 200 mbar down to 30 mbar by an evaporator to remove water to thereby obtain a light yellow crystal. Further, the obtained crystal was dried for one night by a vacuum drier. It was confirmed from an alkali metal analysis using a sodium electrode manufactured by Horiba Ltd., and a liquid chromatograph analysis (LC analysis) using an LC2010 (manufactured by Shimadzu Corp.) that 0.43 g of HOP dilithium was obtained.

Example 10

A HOP Trisodium Hydrogen Carbonate Cocrystal

When 0.78 g of the HOP free form and 0.50 g of sodium hydrogen carbonate were mixed in 20 mL of ethanol, no bubbling from the mixed solution was observed. The mixed solution was stirred at 23° C. for 20 hours. Thereafter, the solid in the mixed solution was filtered to thereby obtain 1.08 g of a white crystal. Further, the obtained crystal was dried for one night by a vacuum drier. It was confirmed from an alkali metal analysis using a sodium electrode manufactured by Horiba Ltd., and a liquid chromatograph analysis (LC analysis) using an LC2010 (manufactured by Shimadzu Corp.) that sodium/HOP was 3. Since when water was added to the solid, bubbling occurred, it was found that a hydrogen carbonate salt remained.

Example 11

A HOP Disodium Hydrogen Carbonate Cocrystal 0.78 g of the HOP free form and 0.33 g of sodium hydrogen carbonate were mixed in 20 mL of ethanol in a flask, when no bubbling from the mixed solution was observed. The mixed solution was stirred at 23° C. for 20 hours. Thereafter, the solid in the mixed solution was filtered to thereby obtain 0.91 g of a white crystal. Further, the obtained crystal was dried for one night by a vacuum drier. It was confirmed from an alkali metal analysis using a sodium electrode manufactured by Horiba Ltd., and a liquid chromatograph analysis (LC analysis) using an LC2010 (manufactured by Shimadzu Corp.) that sodium/HOP was 2. Since when water was added to the solid, bubbling occurred, it was found that a hydrogen carbonate salt remained.

Comparative Example 1

Neutralization of HOP with Sodium Hydroxide 0.39 g of the HOP free form and 20 mL of water were mixed in a flask. A 25% sodium hydroxide aqueous solution was further added so that the added molar number of Na became 3 times the molar number of the HOP free form. Thereupon, the mixed solution in the flask immediately changed in color to brown. The mixed solution was at a pH of 7. Water content of the mixed solution was removed by an evaporator to thereby obtain a black solid. It was found from a liquid chromatography analysis (LC analysis) using an LC2010 (manufactured by Shimadzu Corp.) that the content of HOP contained in 100% by mass of the solid was reduced to 80% by mass, and the decomposition thus advanced. From this result, it was found that in the case where sodium hydroxide was used, color change and decomposition easily advanced and the salt of HOP could not be obtained suitably.

Comparative Example 2

Mixing of HOP and Sodium Hydrogen Carbonate in a Mortar 0.78 g of the HOP free form and 0.50 g of sodium hydrogen carbonate were crushed and mixed for 18 hours by using a magnetic stirrer-driven mortar to thereby obtain a light yellow powder. The powder was a mixture of HOP and sodium hydrogen carbonate, and was not an alkali metal salt.

[Measurement of the Solubility (30° C.) of a HOP Alkali Metal Salt to Water]

Water in such an amount that the HOP alkali metal salt fabricated in each Example remained undissolved was added to 100 mg of the HOP alkali metal salt. The resultant solution was allowed to stand still at 30° C. for 1 hour or more. Then, the solution was centrifugally separated to thereby separate a supernatant liquid and the HOP alkali metal salt remaining undissolved, and thereafter, the supernatant was diluted and the absorbance at 360 nm was measured. The solubility was calculated from the obtained absorbance. The results are shown in the following Table 1. Here, there are collectively shown also data of the saturated solubility of a PQQ free form, PQQ trisodium and PQQ disodium as Reference Examples 2-1, 3-1 and 4-1.

TABLE 1

| Sample | | Saturated Solubility (mmol/L) |
|---|---|---|
| Reference Example 1-1 | HOP free form | 2.9 |
| Example 1-1 | HOP disodium | 290 |
| Example 2-1 | HOP trisodium | 860 |
| Example 3-1 | HOP 2.5 sodium | 780 |
| Example 4-1 | HOP 2.9 sodium | 890 |
| Example 6-1 | HOP tripotassium | 1230 |
| Example 7-1 | HOP dipotassium | 450 |
| Example 8-1 | HOP trilithium | 730 |
| Example 9-1 | HOP dilithium | 230 |
| Example 10-1 | HOP trisodium hydrogen carbonate (cocrystal) | 960 |
| Example 11-1 | HOP disodium hydrogen carbonate (cocrystal) | 230 |
| Reference Example 2-1 | PQQ free form | 1 |
| Reference Example 3-1 | PQQ trisodium | 35 |
| Reference Example 4-1 | PQQ disodium | 7.5 |

From the results of the above Table 1, it was found from comparison of Reference Example 1-1 with each Example that the HOP alkali metal salts and the HOP cocrystals were much higher in the solubility to water than the HOP free form. Particularly, it was found from Examples 3-1 and 4-1 that in the case where the molar number of the alkali metals contained when the whole of the HOP alkali metal salt was regarded to be 1 mol was 2.5 or more, the solubility to water was high. Further, it was found from Examples 10-1 and 11-1 that the cocrystals having carbonate ions were also high in the solubility to water as in the HOP alkali metal salts. Further since in the cocrystals having carbonate ions of Examples 10-1 and 11-1, bubbling was observed when water was added, it was confirmed that carbonate ions remained in the cocrystals.

Further, according to Reference Examples 2-1, 3-1 and 4-1, in PQQ similar in structure of HOP, there was observed no such an improvement of 100 or more times in the solubility that matched that of HOP, and the improving effect of the solubility of HOP was regarded as that characteristic of HOP.

[Storage Stability]

The HOP alkali metal salt fabricated in each Example was subjected to cold storage (4° C.) and room-temperature storage (23° C.) in a solid state, and changes after a lapse of 1 month were visually checked. The results are shown in Table 2.

TABLE 2

| Sample | | Cold Storage (4° C.) | Room-Temperature Storage (23° C.) |
|---|---|---|---|
| Reference Example 1-2 | HOP free form | no change | mingling of slightly red crystal |
| Example 1-2 | HOP disodium | no change | no change |
| Example 2-2 | HOP trisodium | no change | change to brown |
| Example 3-2 | HOP 2.5 sodium | no change | no change |
| Example 4-2 | HOP 2.9 sodium | no change | no change |
| Example 6-2 | HOP tripotassium | no change | change to slightly brown |
| Example 7-2 | HOP dipotassium | no change | no change |
| Example 8-2 | HOP trilithium | no change | change to slightly brown |
| Example 9-2 | HOP dilithium | no change | no change |
| Example 10-2 | HOP trisodium hydrogen carbonate (cocrystal) | no change | no change |
| Example 11-2 | HOP disodium hydrogen carbonate (cocrystal) | no change | no change |

It was found from the results of the above Table 2 that the HOP alkali metal salts and the HOP cocrystals could all be stably handled in the cold storage. It was also found that the dialkali metal salts were stable in both of the cold storage and the room-temperature storage. Further, it was found from Examples 2-2 and 4-2 that when the molar number of the alkali metals contained when the whole of the HOP alkali metal salt was regarded to be 1 mol was 2.9 or less, the stability in the room-temperature storage was more improved. Particularly, it was found from Example 4-2 that the HOP alkali metal salt in which the molar number of the alkali metals contained when the whole of the HOP alkali metal salt was regarded to be 1 mol was 2.9, since being high also in the solubility, could easily be used in various types of applications. Further, it was found from Examples 10-2 and 11-2 that the cocrystals were very stable in both of the cold storage and the room-temperature storage. From comparison of Example 2-2 with Examples 10-2 and 11-2, it was found that the HOP cocrystals in which the molar number of the alkali metals contained when the whole of the HOP alkali metal salt was regarded to be 1 mol was 3 was better in the stability in the room-temperature storage and could more easily be used in various types of applications than the HOP alkali metal salt in which the molar number of the alkali metals contained when the whole of the HOP alkali metal salt was regarded to be 1 mol was 3.

[Cell Activity Test]

Human uterine cancer cells, HeLa cells, were scattered on 96 wells so as to be 1,000 cells/well, and were cultivated in a DMEM (Invitrogen Corp.)+10% FBS culture medium under the condition of a 5% $CO_2$ concentration and 37° C. in an incubator for one night. Thereafter, the HOP alkali metal salt fabricated in each Example was added to the culture medium so that the concentration of the HOP alkali metal salt became 4.9 mg/L and 19.5 mg/L. Further the cultivation was continued further for 2 days, and thereafter, the culture medium was removed from the wells; the well interiors were washed; and the number of the cells in the wells were measured by using a Cell Counting Kit 8 manufactured by Dojindo Laboratories. There are shown in the following Table the results in the case where the number of the cells when no HOP alkali metal salt was added to the culture medium was taken to be 100.

TABLE 3

| Examples | Sample | 4.9 mg/L | 19.5 mg/L |
| --- | --- | --- | --- |
| Reference Example 1-3 | HOP free form | 95 | 103 |
| Example 1-3 | HOP disodium | 116 | 130 |
| Example 2-3 | HOP trisodium | 128 | 121 |
| Comparative Example 1-3 | Reaction product of HOP with NaOH | 105 | 107 |

It was found from the results of the above Table 3 that the HOP alkali metal salts of the present embodiment were high in the cell proliferative activity. Further, the sample prepared under the conditions that the decomposition and color change of HOP advanced and salts could not be obtained suitably was low in the proliferative activity. Further it was presumed that the HOP cocrystals, which conceivably exhibited the same behavior as the HOP alkali metal salts in a dissolved state, brought about the same results as the HOP alkali metal salts.

[Powder X-Ray Diffraction]

The power X-ray diffraction measurement was carried out by using a powder X-ray apparatus of Rigaku Corp. under the condition of Cu—Kα, 40 kV and 100 mA. The results are shown in Table 4, and FIGS. 1, 2 and 3.

TABLE 4

| Sample | | 2θ (°) |
| --- | --- | --- |
| Example 10 | HOP trisodium hydrogen carbonate (cocrystal) | 18.4, 27.5, 30.4, 34.6, 40.8 |
| Example 11 | HOP disodium hydrogen carbonate (cocrystal) | 9.2, 18.4, 27.7 |

TABLE 4-continued

| Sample | | 2θ (°) |
| --- | --- | --- |
| Comparative Example 2 | mixing HOP with sodium hydrogen carbonate in a mortar | 30.3, 34.4 |

Figure 1:
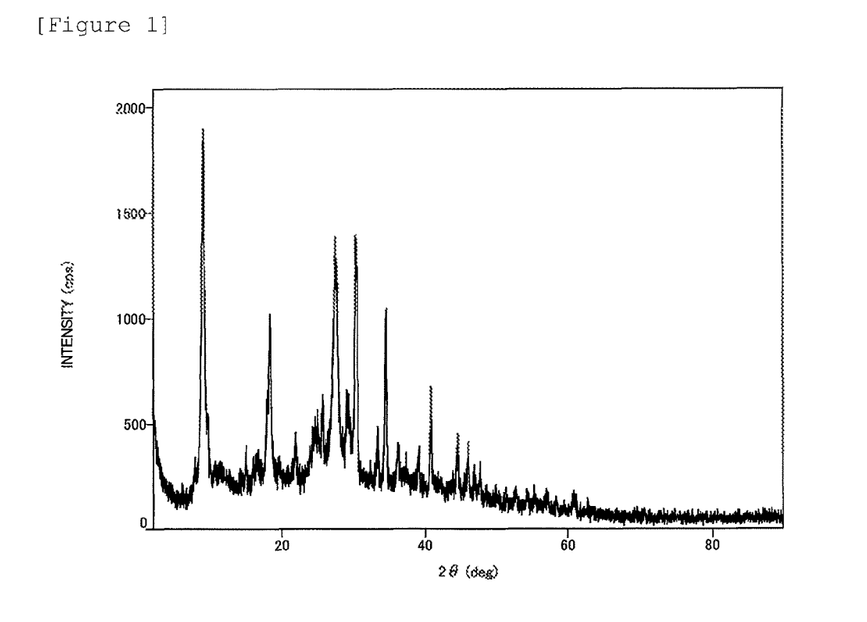
FIG. 1 is a powder X-ray diffraction spectrum of a crystal obtained in Example 10.
Figure 2:
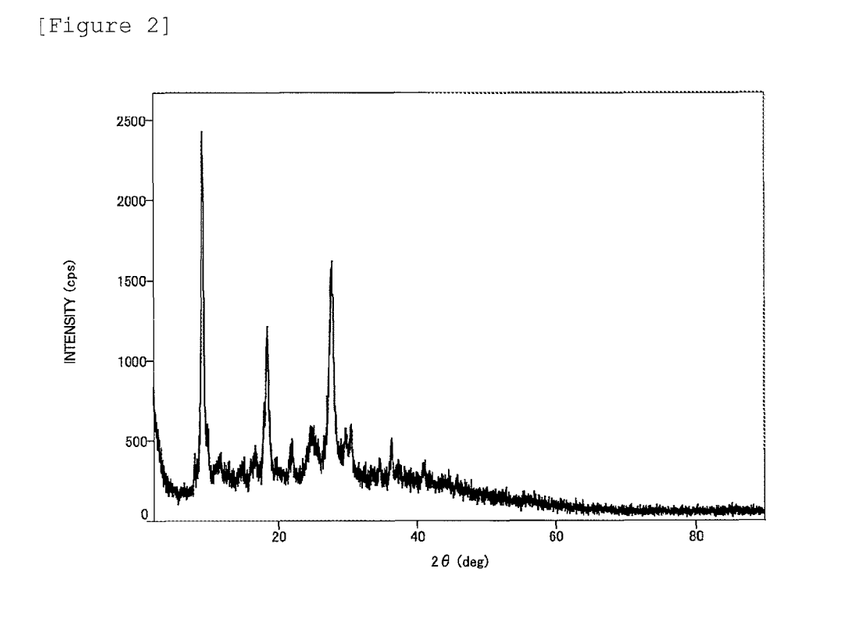
FIG. 2 is a powder X-ray diffraction spectrum of a crystal obtained in Example 11.
Figure 3:
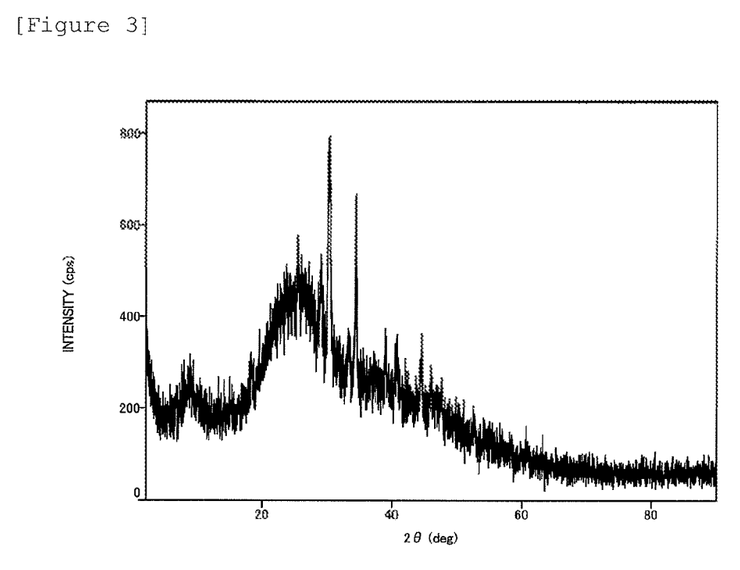
FIG. 3 is a powder X-ray diffraction spectrum of a powder obtained in Comparative Example 2.

It was found from the results of FIGS. 1, 2 and 3 that by mixing HOP and sodium hydrogen carbonate in an alcohol, crystals were formed. It was also found from Comparative Example 2 that although the sample mixed in a mortar had peaks partially overlapping peaks of Example 10, since other peaks were not observed and broad signals were exhibited as a whole, the sample of Comparative Example 2 was a substance having an amorphous component as its main component. From these results, it was confirmed that, unlike the case of physical mixing, mixing in an organic solvent as in the present embodiment caused the crystal formation.

[Chemical Stability]

The HOP disodium fabricated in Example 1 and pyrroloquinoline quinone disodium were tested. 10 mg of the each sample was put in a test tube, and 200 μl of a 10 mass % ascorbic acid aqueous solution was mixed. As a result, no large change in the color of the HOP disodium was observed. By contrast, the pyrroloquinoline quinone disodium changed in the color to black. From this result, it was found that the HOP alkali metal salt was better in the color change resistance than the pyrroloquinoline quinone salt. Further it was presumed that the HOP cocrystals, which conceivably exhibited the same behavior as the HOP alkali metal salts in a dissolved state, brought about the same result as the HOP alkali metal salts.

[Tablet Formation]

10 mg of each of the HOP alkali metal salts and the HOP cocrystals fabricated in Examples 1 to 11 was packed into a mold to the full in a 8 mM tablet form of HANDTAB-100(R) manufactured by Ichihashi Seiki Kogyo K.K., and a force of 10 kN was applied thereto to be thereby able to fabricate a tablet. The HOP alkali metal salts and the HOP cocrystals were thus excellent in the tablet formability, and can suitably be used in applications of oral ingestion and the like.

[Mixing with Oil]

1 mg of each of the HOP alkali metal salts and the HOP cocrystals fabricated in Examples 1 to 11 was mixed in 10 mL of a medium chain fatty acid oil. Thereafter, the mixture was left to stand at 30° C. for 1 day, but no change in color and the like were observed. The HOP alkali metal salts and the HOP cocrystals were thus excellent in the stability in oil, and can suitably be used in applications as a basis to be used for cosmetics and soft capsules, and the like.

The present application is based on Japanese Patent Application (Japanese Patent Application No. 2015-007414), filed on Jan. 19, 2015, the entire contents of which are hereby incorporated by reference.

INDUSTRIAL APPLICABILITY

The HOP alkali metal salt and the HOP cocrystal according to the present invention are high in the solubility, and can be used in the fields of pharmaceuticals, reagents, culture media, foods, cosmetics and resin additives.

The invention claimed is:

1. An alkali metal salt represented by formula (1):

wherein $M_1$, $M_2$ and $M_3$ each independently represent a hydrogen atom or an alkali metal, provided that at least two of $M_1$, $M_2$ and $M_3$ each independently represent an alkali metal.

2. The alkali metal salt according to claim 1, wherein all of $M_1$, $M_2$ and $M_3$ each independently represent an alkali metal.

3. The alkali metal salt according to claim 1, wherein the alkali metal is sodium.

4. A cocrystal, comprising:
the alkali metal salt according to claim 1; and
an alkali metal hydrogen carbonate salt and/or an alkali metal carbonate salt.

5. A method for producing an alkali metal salt of 5-hydroxy-4-oxo-5-(2-oxopropyl)-4,5-dihydro-1H-pyrrolo[2,3-f]quinoline-2,7,9-tricarboxylic acid, comprising:
mixing 5-hydroxy-4-oxo-5-(2-oxopropyl)-4,5-dihydro-1H-pyrrolo[2,3-f]quinoline-2,7,9-tricarboxylic acid with an alkali metal hydrogen carbonate salt and/or an alkali metal carbonate salt in a solvent.

6. The method according to claim 5, wherein the solvent comprises water.

7. The method according to claim 5, wherein the solvent comprises an organic solvent.

8. The alkali metal salt according to claim 2, wherein the alkali metal is sodium.

9. The alkali metal salt according to claim 1, wherein $M_1$ and $M_2$ are each independently an alkali metal.

10. The alkali metal salt according to claim 1, wherein $M_1$ and $M_3$ are each independently an alkali metal.

11. The alkali metal salt according to claim 1, wherein $M_2$ and $M_3$ are each independently an alkali metal.

12. The alkali metal salt according to claim 1, wherein the alkali metal is potassium.

13. The alkali metal salt according to claim 2, wherein the alkali metal is potassium.

14. The cocrystal according to claim 4, comprising the alkali metal salt and the alkali metal hydrogen carbonate salt, wherein the alkali metal hydrogen carbonate salt is present in 2 to 3 mol with respect to 1 mol of the alkali metal salt.

15. The cocrystal according to claim 4, comprising the alkali metal salt and the alkali metal carbonate salt, wherein the alkali metal carbonate salt is present in 1 to 1.5 mol with respect to 1 mol of the alkali metal salt.

16. The method according to claim 5, comprising mixing said 5-hydroxy-4-oxo-5-(2-oxopropyl)-4,5-dihydro-1H-pyrrolo[2,3-f]quinoline-2,7,9-tricarboxylic acid with said alkali metal hydrogen carbonate salt in a solvent.

17. The method according to claim 5, comprising mixing said 5-hydroxy-4-oxo-5-(2-oxopropyl)-4,5-dihydro-1H-pyrrolo[2,3-f]quinoline-2,7,9-tricarboxylic acid with said alkali metal carbonate salt in a solvent.

* * * * *